United States Patent
Thomas

(10) Patent No.: US 7,831,302 B2
(45) Date of Patent: Nov. 9, 2010

(54) MONITORING ELECTRICAL MUSCULAR ACTIVITY

(75) Inventor: Matthew James Thomas, Malvern (GB)

(73) Assignee: Qinetiq Limited (GB)

( * ) Notice: Subject to any disclaimer, the term of this patent is extended or adjusted under 35 U.S.C. 154(b) by 596 days.

(21) Appl. No.: 10/549,732

(22) PCT Filed: Mar. 16, 2004

(86) PCT No.: PCT/GB2004/001120

§ 371 (c)(1),
(2), (4) Date: Sep. 19, 2005

(87) PCT Pub. No.: WO2004/084087

PCT Pub. Date: Sep. 30, 2004

(65) Prior Publication Data
US 2006/0189882 A1 Aug. 24, 2006

(30) Foreign Application Priority Data
Mar. 22, 2003 (GB) .................................. 0306629.7

(51) Int. Cl.
- A61B 5/04 (2006.01)
- A61B 5/0488 (2006.01)
- A61B 5/103 (2006.01)
- A61B 5/117 (2006.01)

(52) U.S. Cl. .................. 600/546; 600/588; 600/591
(58) Field of Classification Search ................. 600/588, 600/546, 591
See application file for complete search history.

(56) References Cited

U.S. PATENT DOCUMENTS

| | | | |
|---|---|---|---|
| 5,383,164 A | 1/1995 | Sejnowski et al. | |
| 5,483,970 A * | 1/1996 | Rosenberg | 600/588 |
| 5,706,402 A | 1/1998 | Bell | |
| 5,776,073 A | 7/1998 | Garfield et al. | |
| 6,167,417 A | 12/2000 | Parra et al. | |
| 6,185,309 B1 | 2/2001 | Attias | |

(Continued)

FOREIGN PATENT DOCUMENTS

EP    1 166 715    1/2002

(Continued)

OTHER PUBLICATIONS

Zhao et al., Independent Component Analysis (ICA) for denoising EMG signal from ECG signal, Jan. 2004, Journal of Zhejiang University (Engineering Science), vol. 38, No. 1, pp. 103-107.*

(Continued)

*Primary Examiner*—Max Hindenburg
*Assistant Examiner*—Emily M Lloyd
(74) *Attorney, Agent, or Firm*—McDonnell Boehnen Hulbert & Berghoff LLP

(57) ABSTRACT

A method of monitoring electrical activity non-invasively (such as uterine activity) which includes applying a localized group of electrodes to a patient's skin and monitoring signals thereon. The electrodes are localized sufficiently such that their muscular signal contributions simulate a single source despite source non-stationarity. The signals are amplified, filtered and digitized. They are then digitally filtered and processed by independent component analysis (ICA) to separate a muscular activity source from other sources. The method may be used to monitor maternal uterine activity, fetal activity and maternal and fetal cardiac activity simultaneously with the aid of additional electrodes and associated circuitry.

19 Claims, 10 Drawing Sheets

U.S. PATENT DOCUMENTS

| | | |
|---|---|---|
| 6,346,887 B1 | 2/2002 | Van Orden et al. |
| 6,424,960 B1 | 7/2002 | Lee et al. |
| 6,524,960 B2 | 2/2003 | Wensel |
| 6,544,170 B1 | 4/2003 | Kajihara et al. |
| 6,751,498 B1 | 6/2004 | Greenberg et al. |
| 6,799,170 B2 | 9/2004 | Lee et al. |
| 2002/0136328 A1 | 9/2002 | Shimizu |

FOREIGN PATENT DOCUMENTS

| | | |
|---|---|---|
| WO | WO 00/54650 | 9/2000 |
| WO | WO 01/27874 | 4/2001 |
| WO | WO 02/088907 | 11/2002 |
| WO | WO 02/096288 | 12/2002 |

OTHER PUBLICATIONS

McKeown et al. "Phase and Tonic Coupling between EEG and EMG Demonstrated with Independent Component Analysis", Journal of Clinical Neurophysiology, pp. 45-57 (2001).

Azzerboni et al. "A New Approach to Detection of Muscle Activation by Independent Component Analysis and Wavelet Transform" Italian Workshop on Neural Nets, pp. 109-116 (2002).

Cichocki et al. "Blind Separation and Filtering Using State Space Models", IEEE, pp. V78-V81 (1999).

* cited by examiner

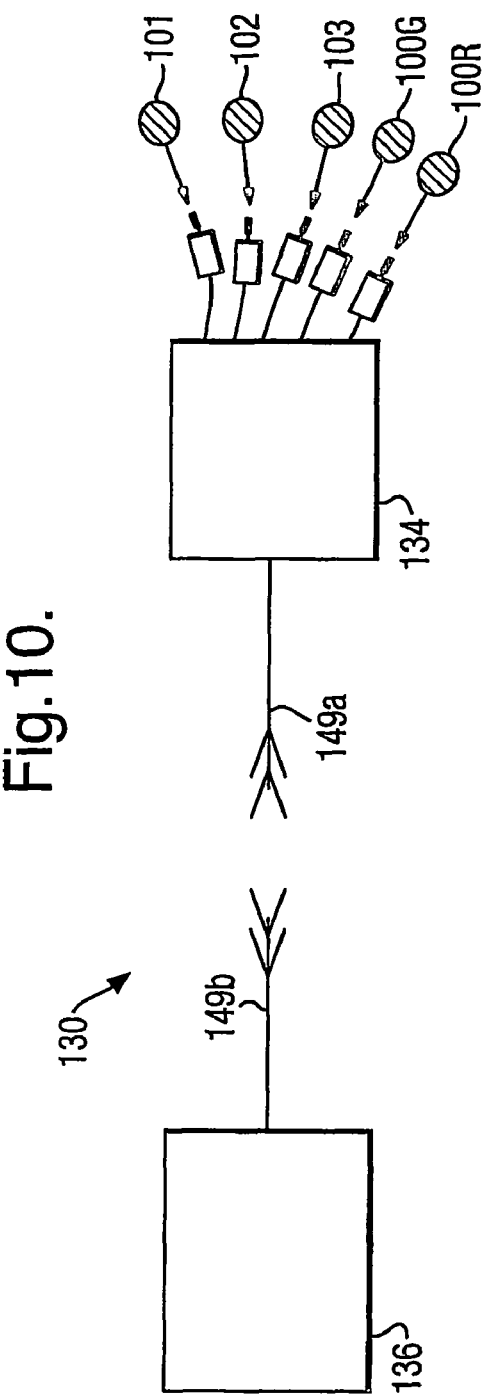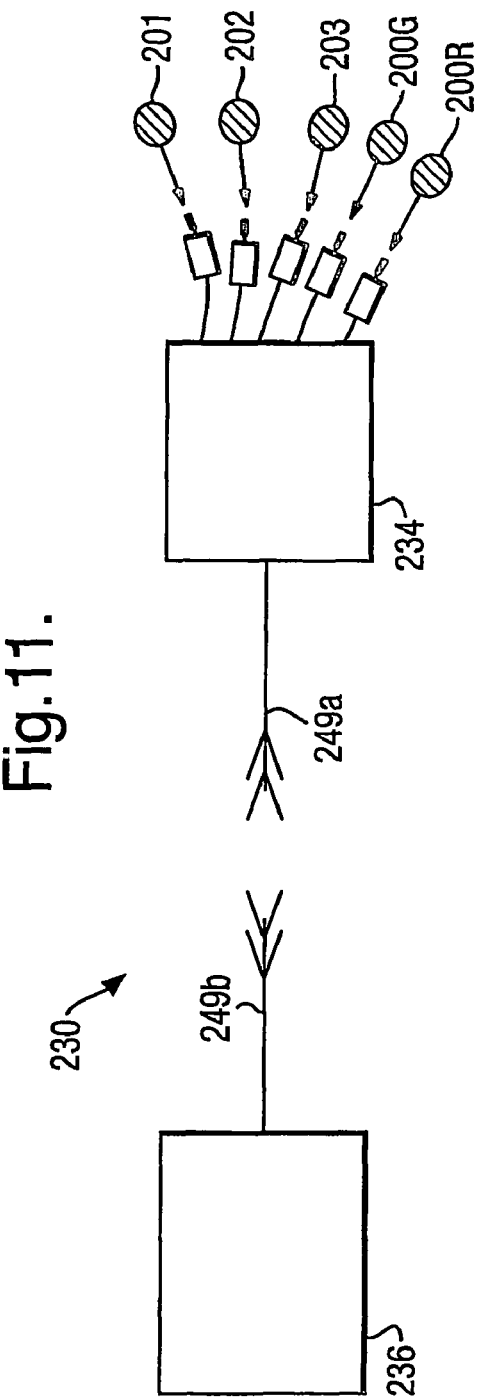

MONITORING ELECTRICAL MUSCULAR ACTIVITY

This invention relates to a method of and apparatus for monitoring electrical muscular activity non-invasively. It is particularly (although not exclusively) relevant to monitoring uterine contractions during pregnancy and labour.

Myometrial activity varies throughout pregnancy and labour. The myometrium—the muscular region of the uterus—is never completely relaxed, and from early gestation it contracts at regular intervals; these contractions are painless and are known as Braxton Hicks Contractions. Up until the end of pregnancy's second trimester, uterine activity is restricted to small, localised contractions, approximately every minute, with larger contractions every 30 to 60 minutes. These larger contractions increase with frequency and intensity throughout the third trimester until the onset of labour. The onset of labour is a subjective assessment based on the frequency of painful contractions and the progressive dilation of the cervix. Preterm labour remains the leading cause of neonatal mortality and morbidity. The current EPIcure study by Costeloe K, Gibson A T, Marlow N, Wilkinson A R, is looking at, 'The outcome to discharge from hospital for babies born at the threshold of viability'. This suggests that almost 50% of babies born in the UK at 23-25 weeks gestation will have significant long-term handicap. Throughout normal labour the intensity, frequency, and duration of contractions increases to 2-4 contractions every 10 minutes with progressive lengthening from 20 seconds in early labour to 40-90 seconds by the end of the first stage of labour. It is described by Llewelyn Jones in, 'Fundamentals of Obstetrics and Gynaecology'. It, is therefore highly desirable to monitor myometrial activity routinely to provide advance warning of premature labour.

Existing methods of monitoring uterine contractions are subjective and principally rely on the frequency of contractions alone to predict onset of labour. Throughout pregnancy this generally relies on symptomatic self-monitoring which lacks accuracy, especially in first pregnancies. During the third trimester a tocodynamometer may be used, this being a pressure transducer which monitors the pressure that the uterus exerts on the abdominal wall. It is strapped around the abdomen and indicates the frequency of contractions and subjectively measures contraction magnitude, which is sensitive to the pressure with which and position to which the transducer is applied.

An intrauterine pressure monitor is a known accurate tool for determining uterine pressure. It is designed to detect and measure intrauterine and amniotic fluid pressure with a catheter placed transcervically into the uterine cavity. It is used to monitor intensity, duration, and frequency of uterine contractions. Despite its accuracy in monitoring the above parameters it involves a bodily invasive procedure and is generally only used in clinical environments. If a reliable non-invasive technique were available then this would be readily accepted by clinicians.

The uterine electromyogram (EMG), or electrohysterogram (EHG), was discovered in 1849. Technical difficulties in obtaining reliable non-invasive EHG measurements, despite many years of research, has led to this being far less commonplace than other electrophysiological monitoring techniques. Many studies have previously recorded the EHG through invasive means and attempted to understand the mechanism of contractile activity, Garfield et al., "Control of Myometrial Contractility: Role and Regulation of Gap Junctions," Oxford Rev. Reprod. Biol. 10:436-490, 1988; Devedeux D, Marque C, Mansour S, Germain G, Duchene J, 1992, Uterine, electromyography: a critical review, American Journal of Obstetrics and Gynecology, VOL. 169, No. 6 pp 1636-1653.

A number of studies have shown that non-invasive transabdominal recordings of the EHG are possible using signal acquisition equipment centered around a differential pair of electrodes, although they acknowledge that signal denoising and removal of unwanted biological artefacts is necessary for successful interpretation. These studies include Simpson N. A. B. et al, 1998 'Changes in uterine electrical activity associated with onset of labour in human pregnancy', Journal of physiology 507.P, 68P; Lenman H, Marque C, 'Rejection of the Maternal Electrocardiogram in the Electrohysterogram Signal', 2000, IEEE Transactions on Biomed. Eng. Vol. 47, No. 8.

To improve reliability of extracting the uterine EMG and to allow its accurate classification, more recent investigations relate to de-noising the contractile wave and characterising the contractions during pregnancy to allow prediction of preterm labour. See Carre P, Lenman H, Fernandez C, Marque C, 1998, 'Denoising of the Uterine EHG by an Undecimated Wavelet Transform', IEEE Transactions on Biomed. Eng. Vol. 45, No. 9; Khalil M, 2000, Uterine EMG Analysis: A Dynamic Approach for Change Detection and Classification, IEEE Transactions on Biomed. Eng. Vol. 47, No. 6.

Further studies have concentrated on the diagnosis of labour based on the uterine EMG, see Rosenberg E, 1996, U.S. Pat. No. 5,483,970, 'Apparatus and Methods for the Diagnosis of Labour'. This reference looks at the uterine EMG across a patient's abdomen. It uses a technique that forms an envelope around the contractile wave to monitor progression of a contraction across the abdomen whilst compensating for any conduction abnormalities. The information obtained is then combined with a direct current offset technique to determine cervical dilation. This apparatus relies on specific placement of electrodes and selection of various coordinate systems for the technique to be successful. The apparatus concentrates on monitoring the progression of labour rather than fetal well-being, although the two can be indirectly related.

There are few investigations suggesting the combination of non-invasive uterine EMG with non-invasive fetal electrocardiography (fECG) for either antenatal screening and monitoring in addition to a tool for monitoring labour events and fetal well-being. Published International Patent Application No. WO 02/096288 (hereinafter "WO/288") suggests an apparatus for the detection and analysis of maternal uterine, maternal and fetal cardiac and fetal brain activity although it is unclear which technique is used to extract which signals and what method in particular is used to extract the fetal electrocardiogram. It refers to (presumably fetal) scalp electrodes for fetal brain activity, and to transcervical and transvaginal as well as transabdominal recordings which indicates it is not completely non-invasive. It suggests that cardiac QRST tracings are obtainable via Doppler ultrasound and pulse oximetry and/or other methods. It also suggests recording transabdominal electrical signals, although the suggested frequency bands of interest for fECG, 1-5 Hz and 20-200 Hz, are not the expected range of 0.5-150 Hz. This range was found during a study associated with International Patent Application No. GB2002/004410 (hereinafter "GB4410") involving over six hundred patients, and is suggested by the American Heart Association Standards for Electrocardiography. However no current standards apply specifically to fECG because of the inability to measure it sufficiently accurately prior to GB4410. In WO/288 the amplitude of cardiac action potentials is stated as 110-140 mV: abdominal electrodes with a 2KΩ electrode skin impedance tend to detect a maternal signal of approximately 200 μV.

Published International Patent Application No. WO 00/054650 also mentions non-invasive fECG and uterine contractions. It discloses an adaptive signal processing filter algorithm (ASPFA) which uses the uterine signal as a noise reference source together with the maternal ECG to produce a fECG compensated for motion artefacts, attributed to the uterine contractions, and maternal ECG artefact. A suggestion is made that surface EMG signals can be used for the monitoring of uterine contractions. Whilst emphasis is placed on the fact that no electrode locations need to be specified, pairs of electrodes need to be located together and reference electrodes for the maternal ECG need to be placed accordingly to aid the ASPFA. There appears to be no explanation of the nature of uterine electromyogram, its method of extraction and/or its clinical significance.

Uterine activity monitoring using maternal abdominal electrodes to develop EMG signals is disclosed in European patent application no. 1,166,715 A2. Received EMG signals are filtered either with an analogue filter or digitally in a microprocessor to monitor uterine activity.

The uterine contraction is said to be instigated at a site of pacemaker cells located at the junction of the fallopian tube and the uterus. Effective contractions occur when what are referred to as bursts are produced at this site. The bursts are most concentrated at the top of the uterus but spread across the uterus, at a rate of approximately 2 cm per second, with the climax of the contraction involving the whole of the uterus as described by Llewellyn Jones, "Fundamentals of Obstetrics and Gynaecology".

As mentioned previously uterine activity occurs throughout pregnancy with action potentials occurring from a very early stage. Various types of properties and waveforms have been attributed to electrical myometrial activity as discussed by Devedeux et al, Am J Obstet Gynecol, 1993, "Uterine Electromyography: A Critical Review", these can be described as (1) Slow Waves or (2) Fast Waves as follows. Slow Waves (1), tend to be associated with abdominal uterine measurements, rather than in vivo measurements, and are therefore assumed to be generated by mechanical artefacts such as skin stretching, their period typically equal to the contraction duration; (2) Fast Waves, Devedeux et al. have separated into a low frequency band (0.1-0.6 Hz) associated with uterine contractions during pregnancy and parturition and a high frequency band (0.6-3 Hz) associated with progressive contractions during parturition only. Devedeux et al conclude that there are no fixed pacemaker sites: instead, like cardiac cells, myometrial cells can be excited by action potentials generated from a neighbouring cell (pacemaker follower cells) or generate their own impulses (pacemaker cells). Also suggested is that each cell can alternate between these two functions. This appears to conflict with Llewellyn Jones, 'Fundamentals of Obstetrics and Gynaecology' although this is concentrating on mechanical factors during childbirth which could be explained by an increased concentration of pacemaker activity in the upper uterus during established labour.

Devedeux et al describe in vivo techniques, i.e. internal measurements made with electrodes attached to the uterus, and detected signals with an amplitude of 12-25 mV, although they conclude that these values are significantly reduced for abdominal recordings. They also conclude that contraction amplitude should not be used as a reference but more emphasis placed on the spectral domain of the uterine Electrohysterogram: this makes it particularly advantageous to de-noise signals efficiently whilst preserving frequency content.

Conventional monitoring of both fetus and mother during labour relies on tools such as Doppler ultrasound and cardiotocography (CTG), which lack sensitivity and specificity. CTG is a device which combines tocodynamometer and Doppler ultrasound to simultaneously monitor contractions and heartrate respectively. The combination of these two measurements allows a measure of fetal well being to be formed based on heartrate accelerations and decelerations, particularly in response to uterine contractions. The Dawes/Redman criterion is an example of a measure of fetal well being used with CTG which looks for accelerations, decelerations, fetal movement, and heart rate variation under specific time criteria. However in conditions such as Diabetes Mellitus this criterion is ineffective due to the absence of a high variation of heart rate. See Tincello D G, et al, 'Computerised analysis of fetal heart rate recordings in patients with diabetes mellitus: the Dawes Redman criteria may not be valid indicators of fetal well-being', Journal of Perinatal medicine. 1998; 26(2): 102-6.

Diagnostic use of CTG appears to have limited effect on perinatal mortality or morbidity in high-risk pregnancies. The Cochrane database suggests there is a trend towards increased perinatal mortality (odds ratio 2.85, 95% confidence interval 0.99 to 7.12) in those assessed by CTG. Although the use of Doppler ultrasound in high-risk pregnancies appears to improve a number of obstetric care outcomes and appears promising in helping to reduce perinatal deaths, it has not been shown to be of benefit in low-risk populations. CTG is sometimes provided for ambulatory monitoring of high risk groups at home although variables such as the tocodynamometer placement, application pressure, uterine wall pressure, subcutaneous fat limitations and data interpretation have a significant impact on its effectiveness. Dyson Donald C et al, 1998, "Monitoring Women at Risk for Preterm Labor", New Eng Journal of Medicine Volume 338:15-19, suggests women with home CTG monitoring have no better outcome than women who have weekly visits by a nurse. This suggests that there may be a requirement for a device which provides a qualitative, non-invasive measurement of the occurrence, spectral content, and magnitude of uterine contractions.

It is an object of the invention to provide a device for non-invasive detection of electrical muscular activity such as that arising from uterine contractions.

The present invention provides a method of monitoring electrical muscular activity non-invasively, the muscular activity being stationary or non-stationary characterised in that the method incorporates the steps of:
a) providing a signal separation technique suitable for separating stationary signals,
b) placing a plurality of low-noise signal electrodes externally upon a patient's skin for detection of muscular activity, the electrodes being localised sufficiently such that:
  i) their muscular signal contributions simulate a single muscular source to the signal separation technique despite any non-stationarity of the muscular source, and
  ii) the number of sources detected by the signal separation technique is not more than the number of electrodes; and
c) applying the signal separation technique to signals received from the electrodes to separate the muscular source.

The invention provides the advantage that it makes it possible to separate a muscular source using a signal separation technique suitable for separating stationary signals despite the muscular activity being non-stationary, which compromises many such techniques as will be described later.

The muscular activity may be uterine activity. The signal separation technique may be based on an instantaneous algorithm as hereinafter defined, and may be independent component analysis (ICA). The step of applying the signal separation technique may apply ICA to processing data derived from signals from the signal electrodes, the data being arranged in successive overlapping blocks such that in pairs of adjacent blocks each subsequent block incorporates a proportion of the data in the respective preceding block, and a correlation scheme is applied to re-order independent sources derived in ICA processing of different blocks to correct for signal swapping.

The step of placing the signal electrodes may comprise placing four or five signal electrodes at and above navel height with respect to an upright patient at positions close to the expected site of pacemaker activity. The signal electrodes may be a first set of signal electrodes and the step of placing the signal electrodes may include placing a second set of signal electrodes upon the patient's skin in positions not localised sufficiently for their muscular signal contributions to simulate a single source to the signal separation technique, and the signal separation technique then employs signals derived via the first set of signal electrodes for monitoring non-stationary muscular activity and signals derived via the first and second sets of signal electrodes for monitoring stationary muscular activity.

The signal separation technique may simultaneously acquire maternal and fetal cardiac activity, and also uterine activity, maternal muscle activity, fetal ECG and maternal ECG. Frequency selective filtering may be employed to facilitate separation of maternal and fetal cardiac activity and uterine activity by limiting the scope for there being more signals than sensors.

In another aspect, the invention provides an apparatus for monitoring electrical muscular activity non-invasively, the muscular activity being stationary or non-stationary, characterised in that the apparatus incorporates:
a) computer apparatus for implementing a signal separation technique suitable for separating stationary signals,
b) a plurality of low-noise signal electrodes placed externally upon a patient's skin (40) for detection of muscular activity, the electrodes being localised sufficiently such that:
   i) their muscular signal contributions will simulate a single muscular source to the signal separation technique despite any non-stationarity of the muscular source, and
   ii) the number of sources detected by the signal separation technique will not be more than the number of electrodes; and
c) processing means for processing signals received from the electrodes into digital signals suitable for application of the signal separation technique by the computer apparatus to separate the muscular source.

The apparatus aspect of the invention may have preferred features equivalent *mutatis mutandis* to those of the method aspect.

Embodiments of the invention will now be described, by way of example only, with reference to the accompanying drawings, in which:

FIG. 1 provides plots of uterine mechanical and electrical activity against time recorded with a tocodynamometer and apparatus of this invention respectively;

Figure 9:
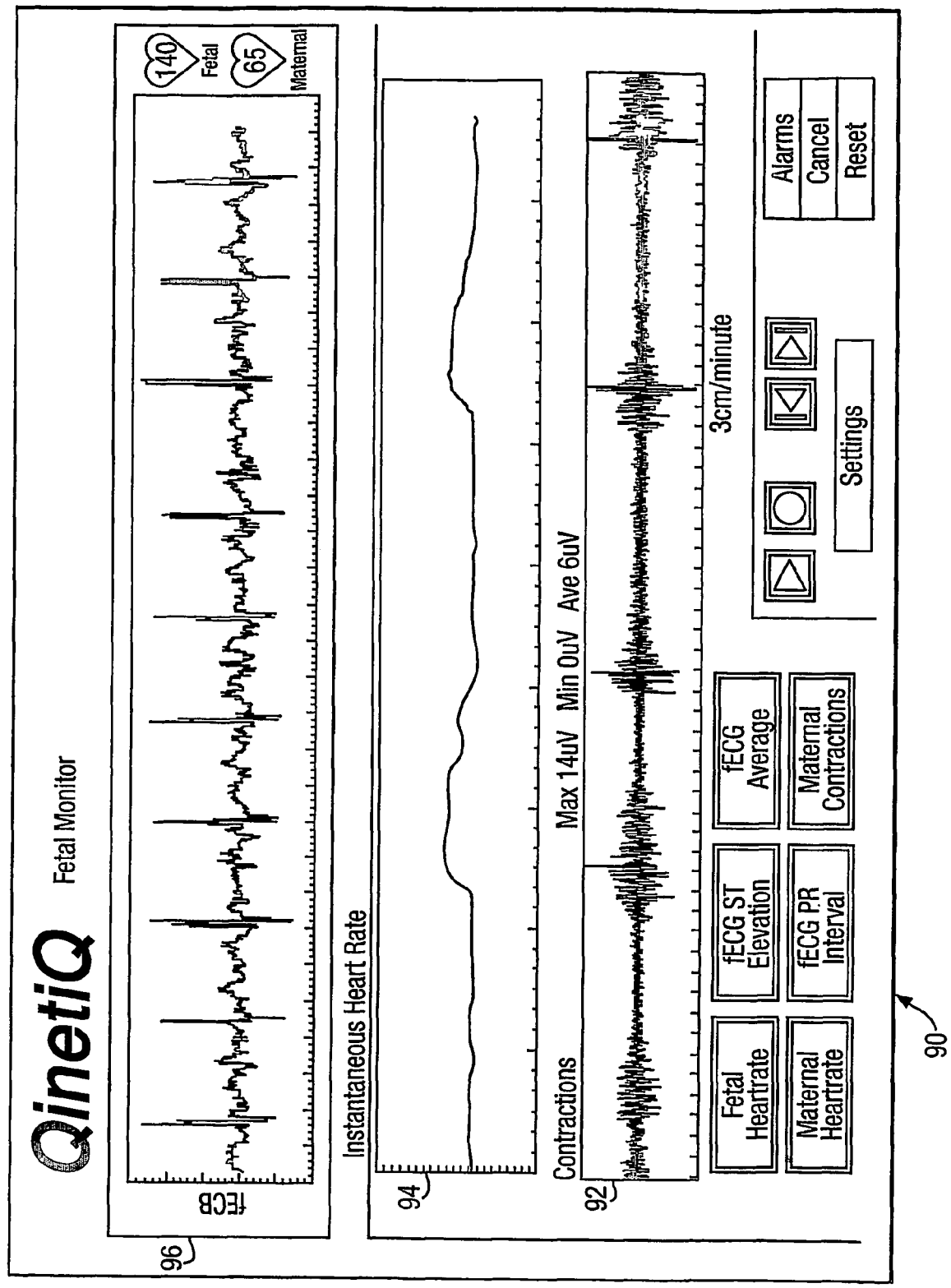

FIG. 9 schematically illustrates a visual display unit showing uterine electrical activity alongside instantaneous heart rate and fECG;

FIG. 10 illustrates signal recording remotely from processing; and

FIG. 11 illustrates use of electrode-mounted buffer amplifiers.

Figure 1:
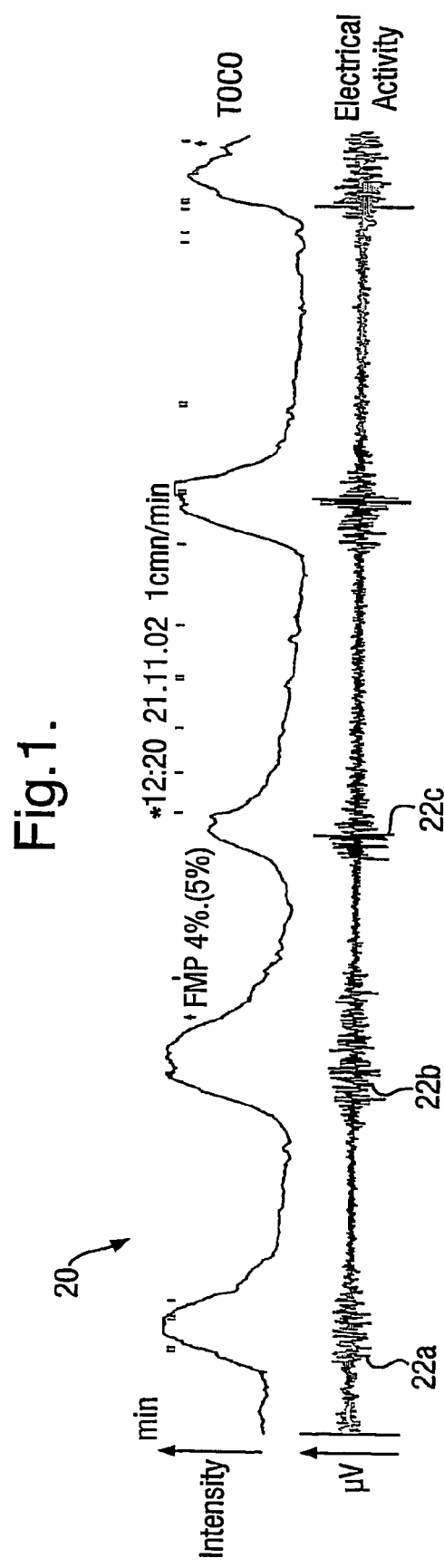
Figure 2:
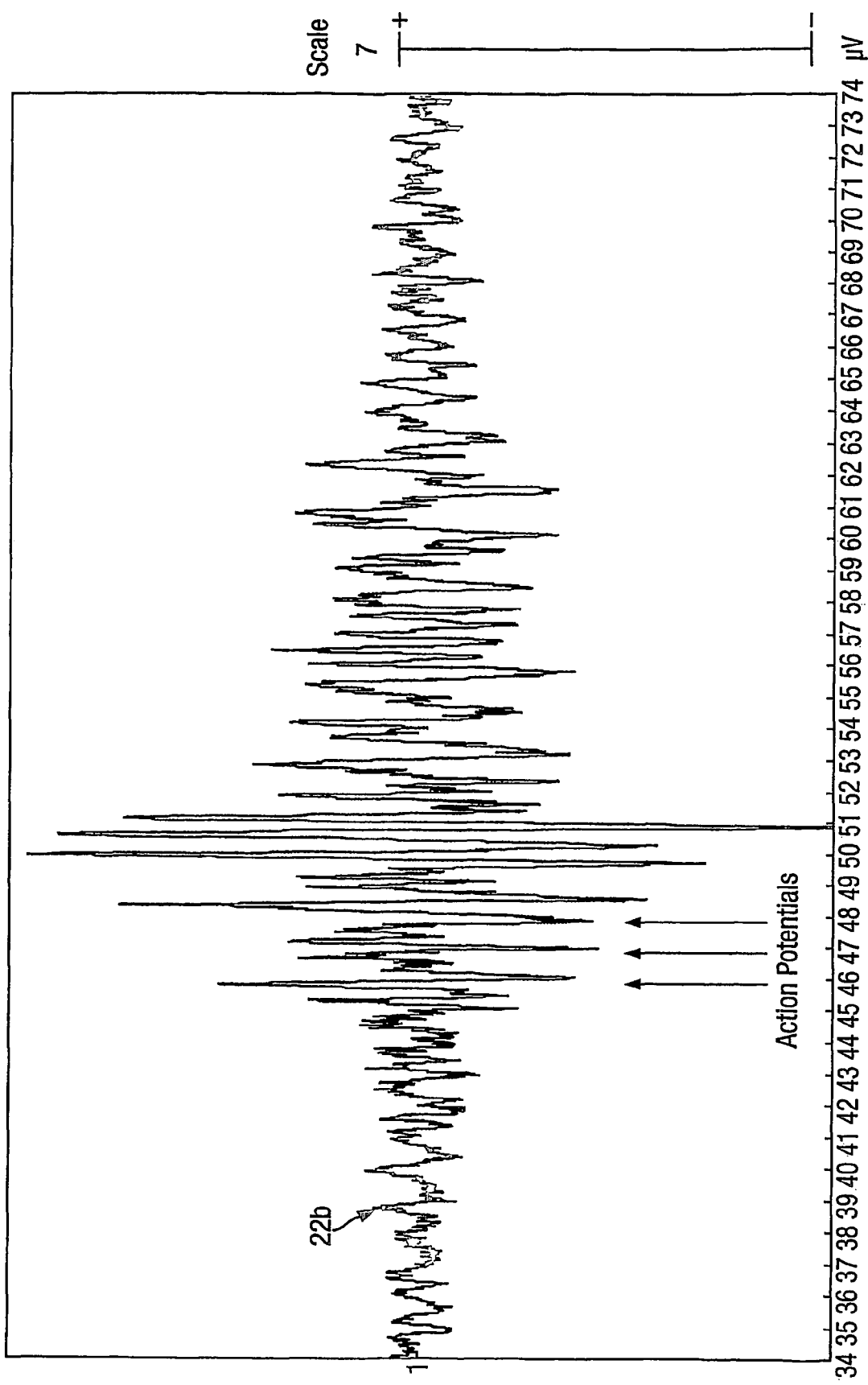
FIG. 2 shows a single burst of uterine electrical activity from FIG. 1 on expanded horizontal and vertical scales.

With reference to FIGS. 1 and 2, a simultaneous recording of uterine electrical activity using this invention and mechanical activity from a tocodynamometer was made during a patient's labour and signal processing applied to extract the electrical uterine activity. The mechanical activity is indicated generally by 20, and the electrical activity by a train of pulses of electrical uterine burst activity such as 22*a*, 22*b* and 22*c*. The two forms of activity are shown plotted against a common time axis. FIG. 2 shows individual action potentials within the single burst 22*b* of uterine electrical activity on expanded voltage and time scales.

Figure 3:
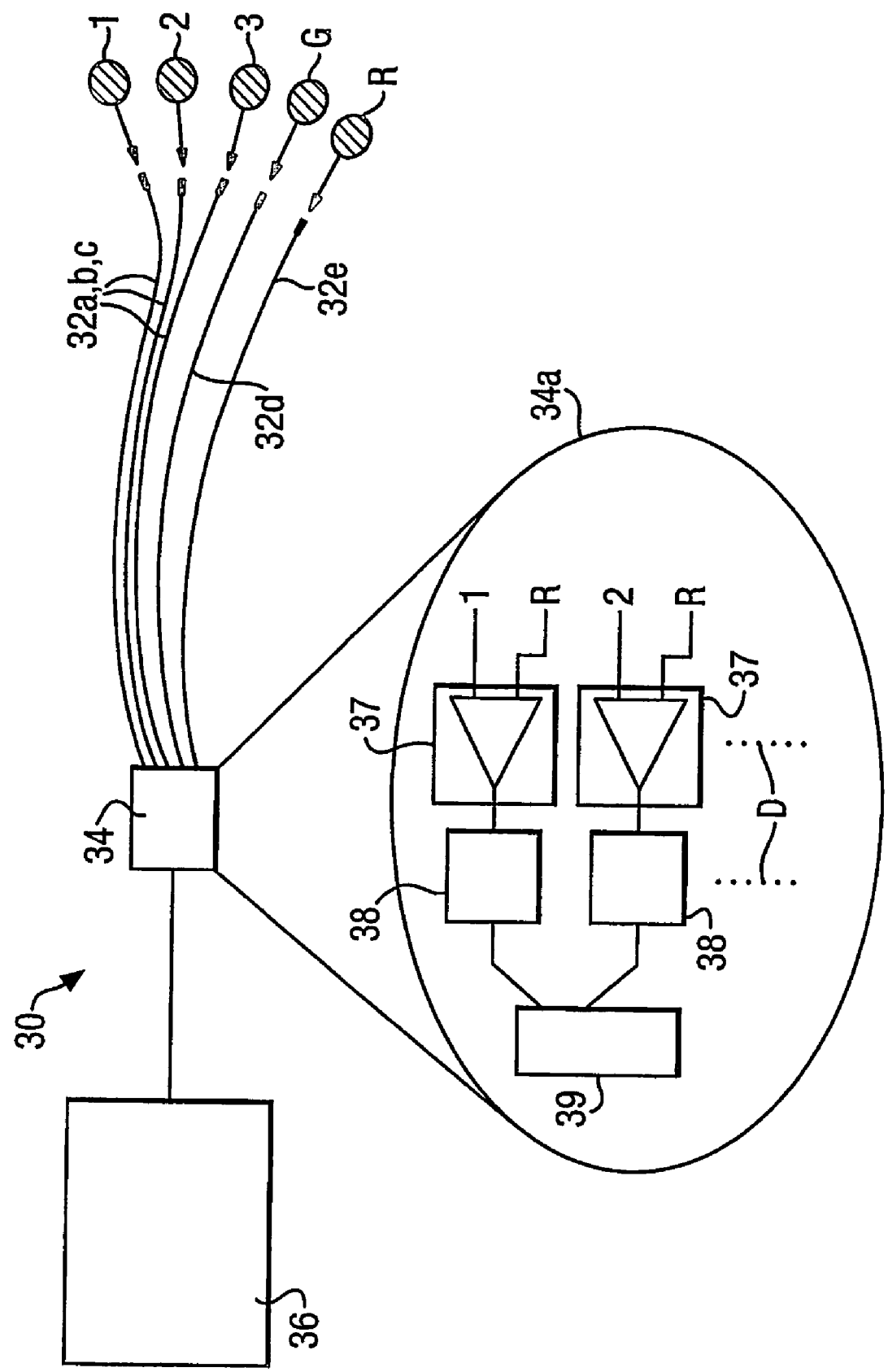
FIG. 3 is a schematic illustration of an apparatus for simultaneously recording uterine activity, fECGs and Maternal ECG in accordance with the invention.

Referring now to FIG. 3, an apparatus suitable for implementing this invention is indicated generally by 30. It comprises a number of electrodes 1, 2, 3, G and R suitable for placing on the surface of a mother's skin and monitoring voltage signals developed there: here G indicates a ground electrode, R a reference electrode and 1 to 3 are signal electrodes. For convenience only five electrodes 1 etc. are shown, but in this example of the invention fourteen electrodes were used as will be described later, G and R electrodes together with twelve signal electrodes numbered 1 to 12 (4 to 12 not shown). The electrodes 1 etc. are connected via respective screened leads 32*a* to 32*e* (collectively 32) to a lead box 34, which is also connected to a computer 36.

The lead box 34 contains processing circuitry for signals from the signal electrodes 1 etc. are shown inset at 34*a*: circuitry is shown for two signal electrodes 1 and 2, dots D indicate like circuitry for other signal electrodes. The circuitry comprises for each signal electrode 1 etc. a respective low-noise differential amplifier 37 and a respective high-pass and low-pass anti-aliasing filter 38. The filters 38 are connected to a common multi-channel analogue to digital converter (ADC) 39. The amplifiers 37 subtract a signal from the reference electrode R from signals from respective signal electrodes 1 etc., and amplify the resulting difference signals. The difference signals are converted to digital signals by the ADC 39, and are then recorded and processed using the computer 36 to isolate the maternal uterine signal and the fECG signal as will be described later in more detail.

A commercially available electroencephalography (EEG) system is suitable for adaptation for acquisition and display of raw input composite data, i.e. signals from electrodes after processing at 30. Here the expression composite refers to the fact that an electrode signal is a mixture of signals from different sources. The computer 36 is that from a portable EEG system (SYS98-Port24-CL) supplied by Micromed Electronics. UK Ltd. It is a battery-powered laptop computer running System '98 EEG recording and analysis software (SYS-98) under Microsoft Windows NT operating system. The SYS-98 software provides a convenient interface from the box 34 to display apparatus (screen, not shown) and to a data storage medium (hard disk). To implement this example of the invention, special purpose bespoke software has been developed and is also run on the computer 36: the bespoke software enables data recorded by EEG-specific software to be read and processed to separate uterine activity and fetal contributions. It also provides for display of parameters derived from such activity and contributions (e.g. duration, intensity, frequency spectrum for uterine activity and fetal heart-rate, PR, ORS, QT intervals for fECG). Operation of bespoke software will be described in more detail later. The type of computer 36 is clearly not critical however, all that is required is that it has sufficient processing capacity for running the recording, processing and display software and sufficient memory for storing the recorded data, processed results and the display itself. Preferably the computer should be portable. Not only does this provide for ease of transfer to patients, but portable computers may be run on batteries in order to isolate them from electrical mains power supply and noise associated with that supply.

The lead box 34 and the computer 36, including a computer display screen (not shown) and recording and display software for raw composite data (as opposed to processed data which is specific to the present invention), as well as their connecting leads are all part of a portable EEG system.

The electrodes 1 etc. are commercially available, disposable, self-adhesive neurology electrodes (type 710 01-K) manufactured by Neuroline®. The principal preferences for the electrodes 1 etc. are that they are low-noise and of a type that is readily attached to a patient in such a way as to result in an impedance at the skin of less than 2 kΩ. Moreover they must be sufficient in number to allow effective signal separation by processing software. Each electrodes 1 etc. with its respective screened lead 32 contributes a respective single, separate, channel of data to a multichannel recording.

The 710 01-K electrodes sold commercially have a 10 cm length of ordinary (unscreened) cable attached to them. This type was selected as the attached cable length is the shortest available. It is preferred that this length of wire is nearer 1 cm, or that the electrodes are attached directly to the screened leads 32 as this would reduce electrical noise further. Disposable electrodes with shorter cable specific to fECG may be made to the same design.

The screened leads 32 are made from 0.9 mm coaxial screened cable of a type suitable for biomedical applications. They should be screened sufficiently to reduce the noise level during fECG recordings to less than 3 μV. Connection is made to the lead box 34 by means of a D-type connector (not shown) having an outer metal case connected to ground for electrical screening. The screened leads 32 connect the signal electrodes 1 etc. to the lead box 34. An outer braided mesh layer of the coaxial cable comprising each screened lead 32 is connected to isolated ground at the lead box 34 and to the metal case of the D-type connector. The earth electrode G is also connected to isolated ground at the lead box 34. This provides a return bias current path to the mother's body for common mode interference which will be rejected by amplifiers 38.

Eight or more signal electrodes 1 etc. are generally sufficient for fECG extraction to provide adequate abdominal coverage and to permit signal separation into sufficient distinct sources. For example, using signal separation as in GB4410, two or three apparently independent sources are generally detected for the maternal heart and typically one or two per fetus. The separation of artefact from uterine contractions is possible from as few as three electrodes as there is a small number of sources and a narrow frequency band of interest. Additional electrodes allow the separation of unwanted artefacts such as those associated with maternal breathing, unwanted electrical interference, etc.

Figure 4:
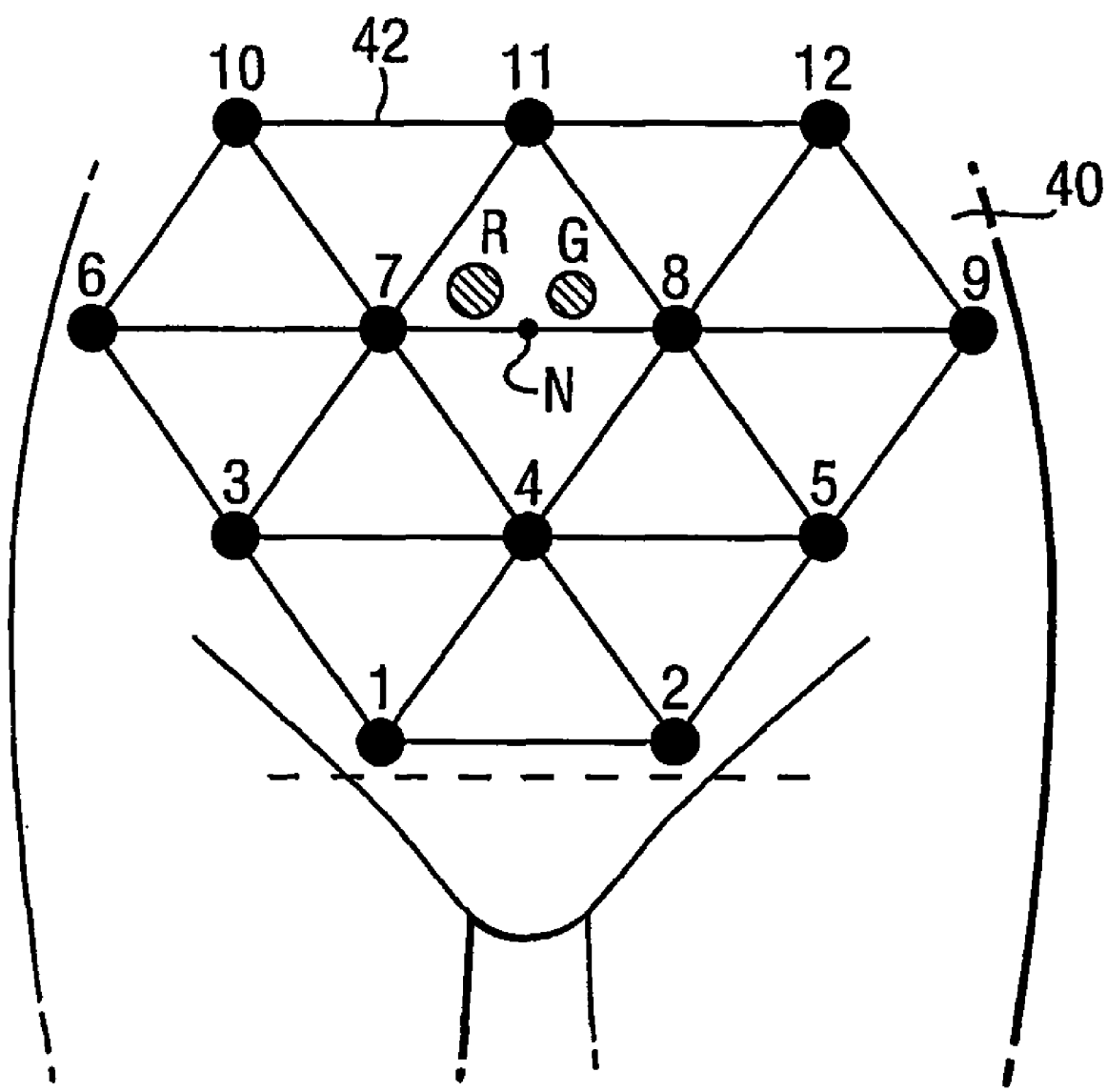
FIG. 4 is a schematic illustration of an abdominal electrode arrangement.

FIG. 4 is an illustration of one possible arrangement of electrodes 1 etc. upon a mother's abdomen suitable for simultaneous monitoring of uterine activity and fetal electrocardiogram (fECG). In this example, twelve signal electrodes 1 to 12, an earth electrode G and a common reference electrode R are all attached to the external surface of a mother's skin 40. Placement is indicated in the drawing by circles indexed with reference numerals of corresponding electrodes. The common reference electrode R and earth electrode G are attached adjacent to the mother's navel N and the remainder are dispersed over substantially the whole of the mother's abdominal area. With respect to the mother's height, electrodes 1 to 5 are below the navel N, electrodes 6 to 9 are level with it and electrodes 10 to 12 are placed above it midway between the base of the sternum and the line of electrodes 6 to 9 that are level with the navel. Electrodes 10 to 12 are at a position which in late pregnancy and labour becomes substantially level with the top of the uterus or fundal height Electrodes 1 to 12 are shown linked by network lines 42 indicating that an approximately hexagonal arrangement of electrodes is conveniently employed for even abdominal coverage. This provides a regularly spaced arrangement of twelve abdominal electrodes with an electrode separation of about 10 cm. In this connection, it is recommended that for uterine monitoring adjacent electrodes are separated by not more than 12 cm. This limit is set to cater for women with larger abdomens. It is not necessary to stipulate a lower limit because the size of the abdomen dictates this by limiting electrode deployment. In order to achieve good uterine and fECG signal separation collectively, the signal electrodes 1 to 12 should preferably not be placed too close together and should involve a wide coverage of the abdomen. A practical placement as shown in the drawing includes coverage from one side of the abdomen to the other and from the pubic hairline to the likely upper limit of the uterus. This latter can be judged from gestation or by following a standard configuration which is sufficient for the maximum height of the uterus which occurs late in pregnancy. It is a feature of this invention that because the electrodes 1 etc. are non-invasive, suitable placement can readily be achieved by a midwife or trained lay person in the case of smaller numbers of electrodes required for uterine activity acquisition.

All leads 32 should be kept as close as possible to the skin 40 and to each other along their entire lengths, in order to reduce electrical and magnetic noise through magnetic flux linkage of loops formed by the combination of mother and leads. Each lead may incorporate a marker in the form of a coloured band to indicate the 12 cm limit between adjacent electrodes to facilitate rapid and accurate electrode placement.

In preparation for attachment and recording, ideally the mother will lie comfortably on a bed with the lead box 34 close by, but touching neither the patient nor the bed frame. She should be allowed to relax for a few minutes to help reduce involuntary muscle activity. This is more necessary for fECG purposes than for uterine monitoring, as the uterine frequency band of interest is narrow relative to the fECG equivalent and is less susceptible to interference.

Voltage signals arising from uterine, cardiac, and other activity are picked up by the signal electrodes 1 to 12, R attached to the skin 40. The signals pass to the lead box 34 via the screened leads 32. The lead box 34 is referred to as a SAM 25R "headbox", and is part of the Micromed Electronics EEG system. The advantage of an EEG headbox as opposed to an ECG lead box, is that the former has superior lower noise electronic circuitry and an increased number of input channels available for use. The input channels are configured for unipolar use.

Further specifications of the SAM 25R lead box of relevance to this example are: touch-proof safety connections, 4 KHz sampling, low-pass anti-aliasing filter with cut-off frequency at 1 kHz, software down-sampled to 512 Hz, pass band from 0.3-256 HZ and 12-bit resolution covering a voltage range of 2 mV.

The SAM 25R lead box 34 is a convenient and commercially available device and was used for those reasons. However, in some respects it has non-ideal characteristics for the purposes of the invention. It has a high pass and low pass filter at its input and an amplifier with a noise level 0.16 µV, i.e. not as low as can be attained (<0.1 µV) when compared with other EEG systems or through the design of a bespoke lead box. The high pass filter might usefully be redesigned to reject frequencies less than 0.1 Hz instead of 0.3 Hz at present, and the low pass filter to reject frequencies greater than ~200 Hz, as opposed to 1 kHz. This would reduce attenuation of low frequency uterine components, reject high frequency noise and improve anti-aliasing.

Detected source voltages range from 7 µV to 250 µV in the frequency range of 0.3 Hz-3 Hz, depending on the stage of pregnancy or labour. Intermittent spike activity (40 Hz-150 Hz) is also regularly observed: it will be separated from uterine activity and fECG with signal processing to be described. It is thought to be associated with abdominal musculature: no significant correlation has been found between intermittent spike activity and contractions other than that of voluntary contraction of the abdominal musculature and diaphragm which may be associated with the onset of a uterine contraction.

Multiple channel inputs to the lead box 34 are used in a unipolar configuration. That is, voltage readings are taken between each abdominal electrode 1-12 and the common reference electrode R. Prior art fECG devices attempted to solve the problem of system noise by taking bipolar readings that attempt to cancel localised noise at the location of the source.

Within the lead box 34, analogue voltage signals from each signal electrode 1 to 12 are fed to one input of a respective differential amplifier 37 and the voltage signal from the reference electrode R is fed to the other. Each differential amplifier 37 therefore outputs an amplified signal proportional to the difference between the voltage developed at the associated signal electrode 1 to 12 and that developed at the reference electrode (R). The resulting amplified signals are filtered by respective anti-aliasing low-pass filters 38 and digitised by the simultaneous multi-channel A/D converter 39. The advantage of using a multi-channel A/D converter 39 is that simultaneous sampling can be arranged on all channels from electrodes 1 to 12, which is a desirable feature for subsequent signal processing. These digitised signals are then passed to the computer 36 for signal processing.

It is to be noted that although a unipolar configuration has advantages, a bipolar configuration is by no means precluded. The latter may be replicated simply by taking differences between digitised unipolar channel outputs, if such a bipolar configuration is required.

In setting up equipment for making uterine activity and fECG recordings it is important to reduce ambient and system noise to as low a level as possible. The following procedure has been found to produce sufficiently low-noise readings:

i). The mother's skin 40 is lightly excoriated using standard abrasive preparation tape (e.g. "Skinprep", manufactured by 3M) and then cleaned with an alcohol- or water-based swab.

ii). The electrodes 1 to 12, G and R are attached to the skin 40 with light finger pressure.

iii). The electrodes 1 to 12, G and R are then connected to corresponding screened leads 32.

iv). The screened leads 32 are connected to the lead box 34 via the D-type screened connector (not shown).

v). The apparatus 30 is battery powered for isolation from the mains supply.

vi). Skin impedance at the electrodes 1 to 12, G and R are measured and any electrode having a skin impedance greater than 2 kΩ is reapplied.

vii). Screened leads 32 are gathered together and maintained close to the mother's skin 40 in order to minimise magnetic pickup.

viii). The apparatus 30 is set to display real-time signals derived from abdominal electrodes 1 to 12, i.e. it has a respective recording channel associated with each electrode.

ix). Possible sources of electrical interference (such as mains) are disconnected if possible.

x). The computer 36 may record composite raw data from the box 34 and save them to its hard disk for further analysis and processing, and/or may continually process and display such data.

Figure 5:
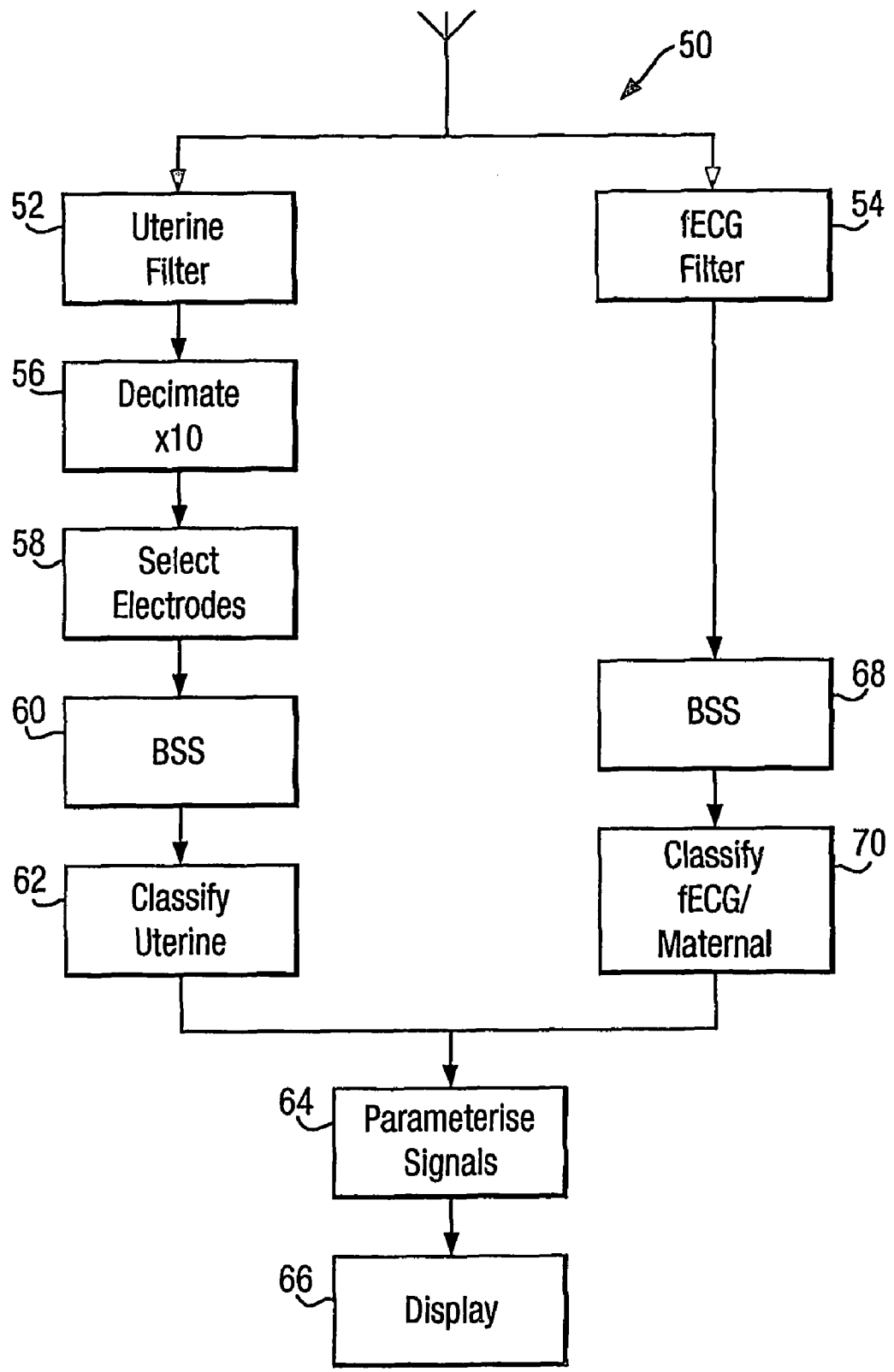
FIG. 5 is a flow diagram of a computer-implemented process to separate uterine and fECG signals from composite signals simultaneously.

Referring now to FIG. 5 and also to FIGS. 3 and 4 once more, signal processing within the computer 36 is indicated generally by a flow diagram of a software-implemented procedure 50. The computer 36 receives, from the lead box 34, twelve separate digital signals associated with respective signal electrodes 1 to 12. The computer 36 processes these digital signals in parallel via two processing threads. Two filters 52 and 54 implemented in software define a uterine thread and a cardiac thread respectively, and all twelve signals are filtered by both in parallel.

The uterine filter 52 isolates uterine activity and is a low-pass infinite impulse-response (IIR) Butterworth filter of 9 taps with a pass band of 0 to 3 Hz, stop-band of 7 Hz with attenuation of 60 dB: it has a 3 dB point of 3.5 Hz and a pass band ripple of 0.01 dB. It does not have high pass filtering, because it is necessary to preserve a low frequency component of uterine activity. Filtering is implemented using a zero phase forward and reverse digital filtering technique of known kind.

For fECG signals, signal sampling should be at a frequency of at least 512 Hz, ten times greater than that required for uterine signals because the latter have much lower frequency content. All signals from the box 34 are sampled by the computer at the rate appropriate for fECG. Signals filtered by the uterine filter 52 are subsequently decimated at 56 by a factor of 10 (90% reduction in data) to an approximately 50 Hz sampling rate to reduce computation and improve signal separation by rejecting unwanted frequency bands. It is convenient to filter and decimate all twelve signals at 52 because it allows selection of signals from different localised groups of electrodes for subsequent processing.

At 58, some of the signals are omitted to concentrate on signals from selected electrodes and not others. In this example only five of these signals are retained in the uterine channel. The five retained signals are those obtained from electrodes 7, 8, 10, 11, and 12 in FIG. 4 after processing at 34. At 60, blind signal separation (BSS) is carried out (as will be described later) to separate signals (or sources) of different types. Subsequently, at 62, the separated signals are classified as uterine or otherwise. The uterine source(s) may be extracted either manually or automatically from other separated artefacts and reconstructed. It is subsequently parameterised at 64 to identify key features relating to uterine activity and displayed at 66.

Similarly, the fECG filter 54 isolates fECG activity: it consists of a high-pass IIR filter of 6 filter taps, and a low-pass finite impulse-response (FIR) filter of 9 filter taps. The high-pass filter is designed using an IIR Butterworth filter with a passband of 2 Hz, stop-band of 0.1 Hz and stop-band attenuation of 120 dB, resulting in a 3 dB point of 1 Hz and a passband ripple of 0.01 dB. The low-pass filter is designed using a Blackman window with a band-edge at 150 Hz. Filtering is implemented using a zero phase forward and reverse digital filtering technique. Digital signals filtered at 54 are processed at 68 to separate signals of different types. Subsequently, at 70, the separated signals are classified as fECG or maternal. Like the uterine signal, the fECG signal is then parameterised at 64 to identify key features and displayed at 66. The uterine signal is displayed alongside the fECG signal.

Blind signal separation or BSS at 60 and 68 will now be described. The expression "blind" indicates that no assumptions are made about signal characteristics or processes which form signal mixtures. It does not rely on foreknowledge of signal characteristics such as arrival direction, frequency, waveform, timing, modulation etc. BSS only requires signals to be statistically independent and for stationarity and linearity to prevail. Stationarity means that signals and their mixing channels do not change with time. Linearity means that the signal mixtures are linear combinations of different signals.

In investigating the separation of uterine and fECG signals using the electrode arrangement shown in FIG. 4, it was found that a well known and popular form of BSS, independent component analysis (ICA), produced useful fECG results but not sufficiently useful uterine results. This was investigated as follows. The uterine signal of interest arises from uterine contractions which are triggered by pacemaker cells which during labour are more concentrated in the upper uterus at the level of electrodes 10 to 12. A contraction propagates relatively slowly down the uterus at ~2 cm/sec, so if a contraction was initiated from the top of the uterus it could take up to ~12 sec to reach the level of the lowermost electrodes 1 and 2 in FIG. 4. It is therefore non-stationary. A version of ICA employed in this example (preferred for other reasons) is limited to stationary signals: signals from electrodes 1 and 12 for example may provide undelayed and delayed versions of a uterine signal respectively, and ICA treats the delayed signal as a different signal to the undelayed signal instead of the same signal apart from relative delay. Similarly a change in morphology of action potentials over the whole myometrium due to different combinations of pacemaker and pacemaker follower cells may result in more sources than sensors, which means ICA will not provide full signal separation.

It is important to use a BSS algorithm such as ICA which is not overly complex so that results can be obtained in real time during labour, or with the shortest delay possible. Most ICA algorithms are addressed to the simplest form of BSS problem referred to as the instantaneous mixing problem: here the signals are assumed to arrive synchronously at each sensor in the array.

Many different algorithms such as ICA are available for solving the instantaneous mixing problem. Unfortunately, an algorithm which is adequate for the instantaneous mixing problem experiences the aforementioned consequences when faced with a more difficult problem which involves relative delay of mixed signals and expressed mathematically as a convolution. This "convolutive mixing" problem can be dealt with as described in International Patent Application No. WO 03/073612 A2, but the processing burden is high and that militates against its use in a real time application.

An alternative and simpler approach to solving the uterine signal delay problem was discovered. Being at the surface of the abdomen remote from the uterus, any electrode receives the uterine signal after a propagation time delay has elapsed from the associated contraction being generated within the mother. It was found that good separation of the uterine signal was obtained by restricting its gathering to a localised group of electrodes: this group was selected to have time delays for receipt of the uterine signal which were sufficiently similar to provide for the signal separation process to treat their uterine contributions as the same signal.

Additionally, using a localised group of electrodes limits the number of uterine sources which may be due to pacemaker cells across the whole myometrium changing the morphology of action potentials. Any grouping of neighbouring electrodes in FIG. 4 will satisfy this. However, in trials conducted to date, the strongest signals and best signal to noise ratio are obtainable from electrodes 7, 8, 10, 11 and 12 in FIG. 4 near/level with and above the navel N, because these electrodes are located relatively close to and substantially equidistant from the position of the top of the uterus during labour where there is a concentration of cells acting as pacemakers initiating uterine contractile waves. The electrodes 7, 8, 10, 11 and 12 therefore receive respective uterine contraction signals without significant delay relative to one another, i.e. any relative delay is not sufficient to compromise results from an instantaneous algorithm such as ICA. These electrodes also receive respective uterine contraction signals from a local group of pacemaker cells rather than several pacemaker sites across the myometrium. This localised group of electrodes limits the effect of non-stationary uterine signals making them simulate stationary signals and restricts the number of sources for the purposes of processing by an ICA algorithm.

An alternative approach to minimising the number of sources due to the convolutive nature of the data is to consider the frequency domain rather than the time domain as this allows time-delays to be modelled through the use of frequency bins. This has inherent problems because a large number of frequencies must be considered together with a permutation/amplitude correction required for each. A simplified approach is discussed by Dapena A. and Serviere C, ICA2001, 'A simplified frequency-domain approach for Blind Separation of Convolutive mixtures'. The main disadvantages of a frequency domain approach is that it is highly computational, although it may prove to be a useful tool in analysing the frequency content of non-stationary uterine activity across the entire myometrium. ICA is a well known analytical technique: see e.g. "Independent Component Analysis—theory and applications" by T-W. Lee, published by Kluwer Academic, Boston (1998). The ICA algorithm used in this example is that disclosed by I. J. Clarke in "Direct Exploitation of non-Gaussianity as a Discriminant", EUSIPCO '98, Rhodes, Greece, 8-11 Sep. 1998. It has been found to be particularly effective. ICA has not previously been applied to extraction of uterine electrical activity. Uterine electromyography has often been investigated using a pair of abdominal electrodes, but ICA ideally requires at least as many sensors as sources, which leads to problems created by multiple pacemaker sites and non-stationary signals. Moreover, successful separation of biological signals by ICA with data recorded over several minutes is difficult due to biological signal mixtures and electromagnetic interference changing with time.

ICA requires data to be processed in blocks that are sufficiently long to ensure that signals are statistically independent. ICA has an ambiguity in that it returns signals it has assigned to temporal independent sources in an arbitrary order, as described by Z. Markowitz and H. Szu, "Blind Demixing Real-Time Algorithm of Piecewise Time Series", Internal Joint Conference on Neural Networks IJCNN '99, pp. 1033-1037, 1999. This is otherwise known as a permutation problem: it makes processing data in blocks difficult because separated signals are returned for a block in usually a different and unknown order compared to those for an adjacent block. It can be referred to as signal swapping, and means that signals cannot be tracked from block to block. It is dealt with in this example by introducing prior data from each data block to a respective immediately following block. To overcome the signal swapping problem, pairs of adjacent blocks $X_1$ and $X_2$, $X_2$ and $X_3$ etc. are overlapped sufficiently so that e.g. $X_2$ contains samples correlated with those of $X_1$. A correlation scheme is then applied to re-order independent sources determined by ICA for each block to correct for signal swapping. This assumes that no significant artefact is introduced in $X_2$ which would alter a mixing matrix M generated in ICA and change independent sources so that the correlation scheme would fail. The likelihood of this occurring can be reduced by using an overlap, for example, 50% of the block length, though the precise overlap is not critical and may be optimised by experiment. The result is a continuous signal on a single channel for the signal of interest, i.e. not swapped between channels.

Consequently, to carry out ICA for the uterine signals, recorded data from 58 was segmented into successive smaller blocks of 500 samples (sample window). Each sample was a snapshot of data, i.e. it consisted of five simultaneously recorded signals, one such signal from each of the electrodes 7, 8, 10 to 12. Each data block was approximately 10 sec long with 50% overlap or redundancy; i.e. the first half of each block was the second half of its predecessor. Each block therefore shared its first and second 250 samples with preceding and succeeding blocks respectively. The blocks were processed individually by ICA in the computer 36. The incoming data stream first fills the 500-sample window with a block of data and the ICA algorithm calculates a de-mixing matrix in a known manner. The de-mixing matrix is then applied to incoming data one sample (snapshot) from each sensor at a time as each sample streams into computer memory. In the mean time the window is updated on a 'first in first out' basis with the next block of data, from which a new de-mixing matrix is calculated. The new updated mixing matrix was calculated when 50% of the window length had been updated to allow the correlation scheme to be implemented. This technique relies on the de-mixing matrix remaining unchanged for at least the time it takes to calculate the updated mixing matrix. The reduced window/block size of 10 sec and 50% overlap proved effective although other values may be used. The above scheme is employed because the mixing matrix for the sliding window cannot currently be recalculated at the same rate as the sampling interval updates it due to computational limitations. However, with improved computation of the ICA algorithm, and further algorithm-based schemes to address signal swapping, it will become possible to update an ICA-derived de-mixing matrix in response to input of each sample or at least in a non-critical time frame i.e. <1 second for uterine contractions. This will remove the need to rely on the assumption that the de-mixing matrix remains unchanged until the new de-mixing matrix is calculated. A technique which removes the need for this assumption is the subject of patent application No. GB0236539.4 dated 14 Nov. 2003.

In what follows a particular example of the implementation of an ICA algorithm is described that has been found to be advantageous, although it is not essential to use this particular technique. It is described in I. J. Clarke in "Direct Exploitation of non-Gaussianity as a Discriminant", EUSIPCO '98, Rhodes, Greece, 8-11 Sep. 1998. ICA will now be described in more detail. It is used at 60 to analyse signals from five electrodes 7, 8, 10, 11 and 12 for uterine monitoring and signals from all twelve electrodes 1 to 12 for fECG monitoring. ICA defines a separation method for observed composite data variables $x_i$ (i=1 to n) based on the assumption that each is a linear or non-linear mixture of some unknown latent sources $s_j$. The mixing process is also unknown and the sources are assumed to be statistically mutually independent and non-Gaussian.

An index i is given by the electrode references 1 to 12 (FIG. 4) associated with the relevant data; i.e. electrode i gives rise to a signal which is processed by the lead box 34 and as shown in the flow diagram 50 (up to but not including BSS) to provide a signal $x_i$, where i=1 to n and n=5 (uterine) and n=12 (fetal) in this example. Each signal $x_i$ was digitised at 34 and so comprises a number (say m) of time samples of recorded data. The m time samples for signals associated with each of n electrodes collectively form an m×n data matrix X of processed digital signals. From the data matrix X the ICA algorithm generates a mixing matrix M and a set of n independent sources $s_j$ (j=1 to n) such that each sensor output $x_i$ can be written as a different linear combination of $s_j$ i.e.:

$$\underline{x_i} = \sum_{j=1}^{n} m_{ij}\underline{s_j} \text{ or, as matrices: } X = SM \quad (1)$$

where X is a matrix whose columns are the n sets of processed electrode signals $x_i$ and S is an m×n matrix whose columns are the set of n independent sources $s_j$. A de-mixing matrix W is now defined which is the inverse of the mixing matrix M, i.e. their product is the unit matrix. In this way the composite data X is separated into different independent sources $s_j$ of interest.

The demixing matrix W can be estimated in two stages, the generation of an orthonormal basis e.g. using singular value decomposition (SVD), and a refinement to make them statistically independent. In the first stage, an SVD can be carried out on the (m×n) matrix X. SVD is a well-known decorrelation and normalising technique. The SVD of a matrix X can be expressed as:

$$X = U\lambda V \quad (2)$$

where U and V are orthonormal (m×m) and (n×n) matrices respectively and λ is an (m×n) diagonal matrix with positive real diagonal elements (the singular values in SVD), arranged in decreasing order.

The columns of U are left orthonormal singular (temporal) vectors of X and they contain information about sources $s_j$. The rows of V are right orthonormal singular vectors of X and they contain information about the spatial distribution of the sources $s_j$ (i.e. magnitude at each sensor). The singular values λ are related to the power levels associated with individual temporal singular vectors.

In general, the estimated signals (contained in the columns of U) are not fully separated. The reason for the failure of SVD to separate the signals is that it constrains both the matrices U and V to be unitary. This is inherent in the SVD methodology as it is a second order decorrelation method, which is intended to remove all similarities between signal pairs in a set of signals. Mathematically, this means that decomposed vectors are made orthogonal. In many "real-life" signals, the spatial information (contained in the rows of V) of the signals will be similar (correlated) and so a solution that makes them dissimilar will not succeed in separating them.

the source signals by a hidden rotation matrix. Determining this missing rotation matrix necessitates the use of higher order statistics (HOS). The use of HOS to separate unknown, independent signals is often referred to as independent component analysis (ICA) and this is the second stage in the separation process.

The matrix X can be expressed as:

$$X = URR^T \lambda V \quad (3)$$

Where R denotes an (m×m) rotation matrix and $R^T$ its transpose. R is unitary, such that $RR^T$ is equal to an identity matrix I. The rotation matrix is determined using estimated signals contained in U.

In general, for q signals, where q≦m, R denotes a (q×q) matrix, U denotes a (m×q) matrix, λ denotes a (q×q) matrix and V denotes a (q×n) matrix. In Equation (3), the estimated signals are contained in UR and estimated mixing is defined by $R^T \lambda V$.

The separation process may treat the signal mixing process as a complicated combination of rotation, stretching and shearing. Decorrelation removes the stretching and shearing effects, so that only a rotation needs to be applied to separate the signals. Rotation cannot apply shearing or stretching, and thus cannot counteract decorrelation.

The method for the computation of R is described in the I. J. Clarke reference previously given, and other techniques are also known. This model assumes that the sources $s_j$ are point sources, which is clearly not the case for physiological sources such as uterine action potentials which are of finite extent. It is a consequence of the ICA calculation in these circumstances that multiple, separated sources are apparently found for the uterine activity with different morphology instead of a more convenient single source. If twelve abdominal sensors were to be used for uterine monitoring as shown in FIG. 4, from three to seven apparent sources of uterine activity would be found by ICA, the number depending on factors such as electrode/source proximity, extent of contraction across the uterus and electrical conduction to the surface. The additional sources tend to be those associated with maternal ECG, fetal and electrode movement artefact and electromagnetic interference. While twelve electrodes are recommended for fECG separation, as has been said five may be used for uterine activity separation in this example. Using this number of electrodes reduces problems associated with non-stationary uterine activity seen across the whole abdomen and reduces uterine activity to a single source; it allows additional sources not representing uterine activity to consist of artefacts such as maternal/fetal ECG, motion artefact and electromagnetic interference.

Figure 6:
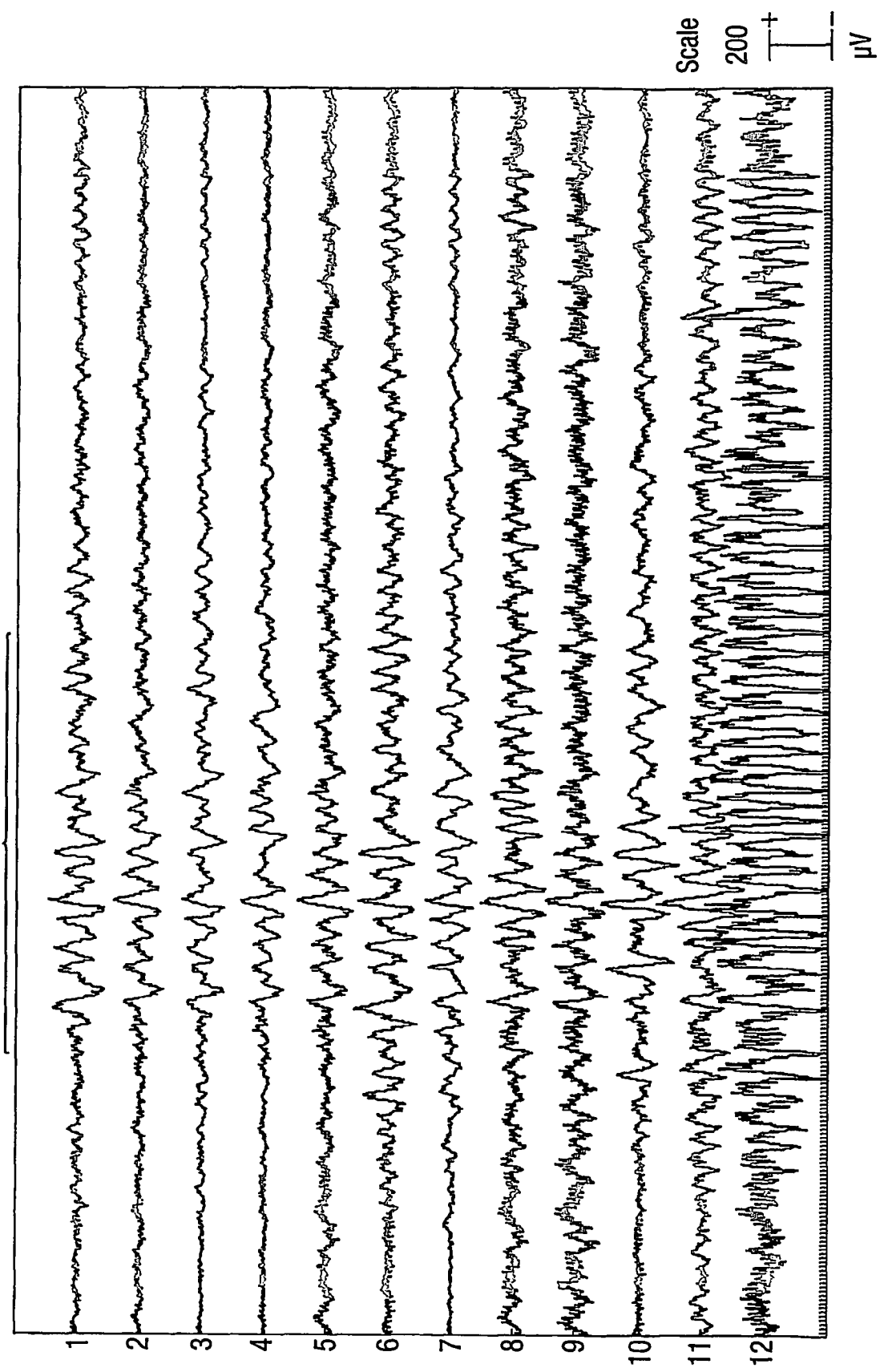
FIG. 6 illustrates composite signals recorded using the electrode arrangement shown in FIG. 4.

For the purposes of illustrating the problems which arise out of use of non-localised electrodes in monitoring uterine activity using ICA, twelve signals recorded over 30 minutes during a singleton (single fetus) pregnancy during early labour using electrodes as shown FIG. 4: the signals were filtered at 52 in a frequency band from 0.3 to 4 Hz suitable for extraction of uterine activity. A 130 second enlargement of these signals is shown in FIG. 6: the signals are numbered on the left 1 to 12 to indicate the associated electrode in each case. In all twelve signals approximately 45 seconds of uterine activity is visible in regions vertically below a curved bracket 80, although it is corrupted by a maternal ECG contribution; this contribution can be seen on signal 10, where it is strongest and is identified by small spikes on low frequency action potentials of the uterine signals. It can also be seen on a number of other signals It is also corrupted by another muscle/movement artefact associated with labour shown in signal 12 which occurs beyond the uterine activity or contraction below 80. FIG. 6 shows that information relating to uterine contraction may be difficult to interpret because of mixing of signals of different types from different sources.

Figure 7:
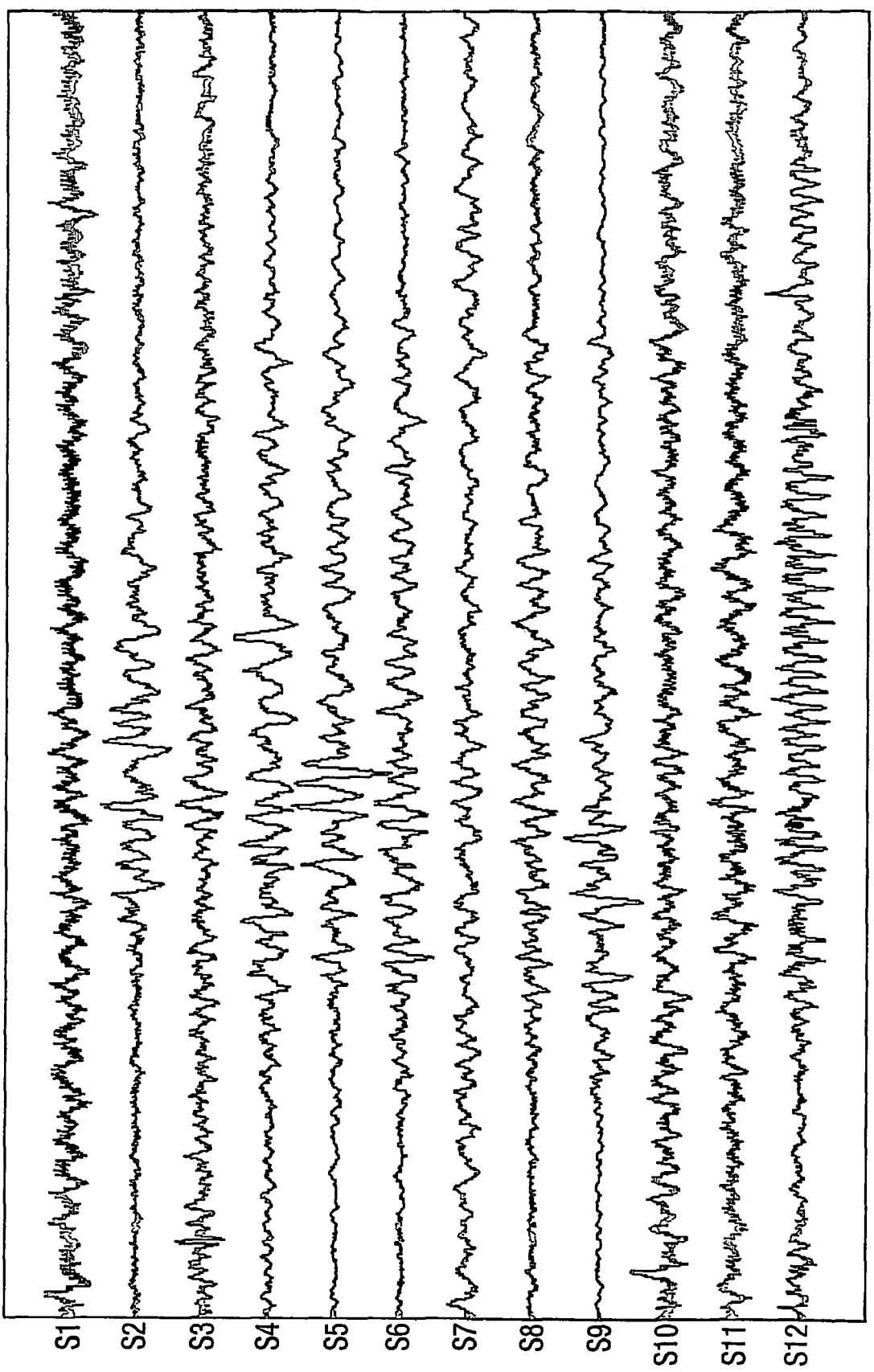
FIG. 7 illustrates independent signal sources separated from composite signals using the process of FIG. 5.

Referring now to FIG. 7, ICA was applied to the signals 1 to 12 of FIG. 6 and results are shown as separated sources S1 to S12 (marked on left): these sources are shown on a normalised vertical scale (not shown) so that each source has unit power, and they are plotted against a horizontal time axis (not shown). The form of the uterine signal is well known and shown in FIG. 2, which is compared with each of the separated sources S1 to S12. Sources S2 to S6 inclusive, S8 and S9 all show structure similar to FIG. 2 with relative delay increasing from S2 to S9: this shows that ICA indicates seven uterine sources are present (more conveniently there would only be one). As has been said this is attributed to non-stationarity of uterine activity. Also, action potentials may also be triggered simultaneously from different pacemaker sites on the myometrium. This is a further mechanism for the creation of more uterine sources. Both of these effects are mitigated by the use of a subset of the available electrodes 1 to 12 as described earlier.

S1, S10 and S11 are a maternal ECG and breathing artefact separated into separate sources: this artefact was visible on all of the signals 1 to 12 shown in FIG. 6. ICA has separated into a single source S12 a large artefact, which persisted beyond the duration of the uterine contraction giving rise to the uterine signal. S12 contributed predominantly to signal 12 in FIG. 6, but it also interfered with other such signals.

Figure 8:
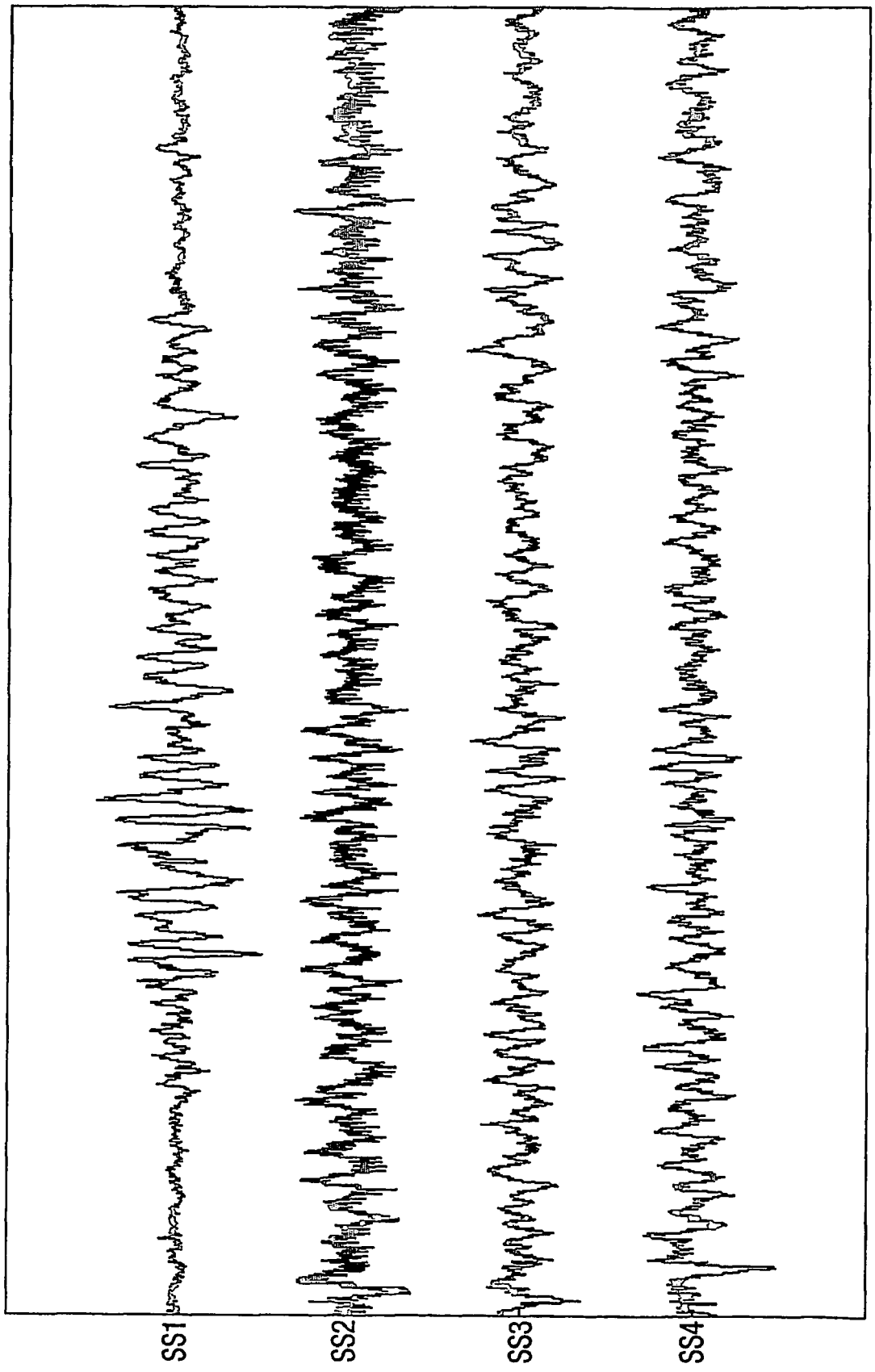
FIG. 8 is equivalent to FIG. 7 but corresponds to a reduced number of localised electrodes positioned to desensitise processing to signal non-stationarity.

FIG. 8 illustrates the improvement obtained by restricting the locality of electrodes used for the uterine signal. It is equivalent to FIG. 7 except that only four sources are shown. Although use of signals derived from five signal electrodes was described earlier, in the case of FIG. 8 only four such signals were used, these being derived via electrodes 7, 8, 10 and 11 in FIG. 4. It should be added that any number of electrodes can be used in this regard so long as they are sufficiently localised.

Four sources are shown referenced on left SS1 to SS4. Comparison of these sources with FIG. 2 shows that uterine activity appears in SS1 only. In other words uterine activity has been separated into a single source SS1 Without any artefact originally shown in FIG. 6. Source SS2 has the periodicity of maternal heart rate and breathing, and so the maternal ECG and breathing artefact is also separated in the single source SS2. A remaining unidentified artefact results in two apparent sources SS3 and SS4: it is not associated with contractile activity because there is no similarity to SS1 or FIG. 2, and it extends beyond the duration of uterine activity or contraction in SS1 which was monitored in parallel with a tocodynamometer for verification.

FIGS. 6, 7 and 8 demonstrate that it is straightforward to choose a localised set of electrodes to which propagation delays for the uterine signal are sufficiently similar for ICA to treat contributions to the uterine signal from these electrodes to be one signal. One can even select localised groups on trial and error basis and see how many uterine signals are separated in ICA in each case. The criterion is that ICA should preferably separate only one uterine signal, although multiple uterine sources may be selected and reconstructed at each electrode location with unwanted artefact removal.

In order to extract the uterine contraction from the separated sources, the output of each electrode can be reconstructed using only the contribution from uterine activity. That is, each electrode trace is first modelled as a mixture of sources, and then reconstructed using only those sources of interest $$(x_i(m) = \sum_j m_{ij} s_j,$$

j being restricted to the index associated with particular separated sources). This gives rise to modified signals in which the uterine activity is readily apparent and other sources have been suppressed.

In this embodiment of the invention, selection of the required sources is made manually and implemented using a source-selection icon displayed on the computer 36 next to each separated source. Each icon may be toggled between a "no" indicator, meaning discard the source and a "yes" indicator, meaning make use of it. This can be automated to display uterine activity without operator intervention. Automation may use an adaptive threshold peak detection routine to detect action potentials of uterine activity. It would adapt to the statistics of each separated source to maximise the likelihood of detecting envelopes of uterine activity. Whilst monitoring during pregnancy this process may take several minutes until a contractile source is found and until then all channels would need to be monitored. Once a contractile source is identified it may be monitored using this technique to allow each burst of contractile activity to be marked by a window for further analysis; such analysis may be spectral analysis to differentiate between two categories of fast wave uterine activity referred to as $Fast_{LOW}$ and $Fast_{HIGH}$, which can be used as indicators for onset of labour.

To extract fECG signals at 68 in FIG. 5, the procedure is as for uterine activity monitoring except that signals derived from all twelve signal electrodes 1 to 12 are used, i.e. across the whole of the patient's abdomen. Compared to uterine signals, signal separation in fECG is not complicated by non-stationarity, because the fetal heart is small and consequently the fetal electrocardiogram can be modelled as a point source surrounded by a homogeneous conduction medium. The fECG therefore has stationarity for the purposes of ICA.

Although noise reduction is important in enabling uterine activity to be extracted readily throughout pregnancy from electrode signals, an apparently noisy signal may still prove useable. This is because the ICA technique will isolate separable noise for discarding. However, separable noise is not always distinguishable from inseparable noise in electrode signals, and so it is important to reduce noise as far as possible.

Abdominal surface intensity maps may be generated from separated sources by shading a map of geometrical locations of signal electrodes according to the strength of the coefficient $m_{ij}^2$ of the desired source number j (or combination of sources) at each signal electrode i. Brighter areas are used to Indicate higher levels of signal strength, this allows the position of multiple uterine sources, which may have resulted from the non-stationary uterine signal, to be identified at their respective locations across the abdomen. This may provide an insight into progressive and non-progressive contractions and also further analysis of propagation mechanisms across the myometrium.

It is not essential to carry out signal separation using ICA, but this technique and its I J Clarke version referred to above are preferred. Other signal separation algorithms are known, see for example International Patent Application No. WO 03/073612 A2 which reviews the prior art on instantaneous and convolutive mixing in addition to providing a version of convolutive mixing. Standard band pass frequency filtering has been used in the prior art to view the uterine activity particularly in labour when the signal is at its strongest. However, the ICA/Clarke technique is preferred for detailed analysis of uterine activity throughout pregnancy and during labour where there is considerable unwanted artefact. Substantial frequency filtering may remove or degrade signals of interest due to overlapping frequency ranges of a desired signal and an artefact. In addition, wavelet denoising schemes have been used, as discussed previously, which (unlike BSS) rely on prior knowledge of the interfering artefact.

Using prototype apparatus it has been found that it takes approximately five minutes to apply a full array of signal electrodes 1 to 12 and ground and reference electrodes G and R and begin monitoring. However, as described above, for acquisition of uterine activity fewer signal electrodes are successfully employed, as few as three. Moreover, improvements to mathematical signal processing techniques and hardware may allow the number of electrodes to be reduced below eight for fECG acquisition, which involves a wider frequency spectrum and hence more possible sources.

An electric guard potential may be applied to shielding of the screened leads 32. It reduces the effects of lead capacitance and of mismatch between input capacitances. It increases the common mode noise components of detected signals that are rejected by differential amplifiers 37. Although the guard potential may be similar to the signal voltage of interest, the shielding must be driven from a low impedance source, such as for example a voltage follower driven by the signal of interest.

FIG. 9 schematically shows a display monitor 90 suitable for use in displaying sources separated simultaneously as described above. The monitor 90 shows separated electrical uterine activity 92, and instantaneous heart rate 94 derived from an fECG 96. It is extremely useful to be able to monitor maternal and fetal parameters in this way, because during labour the fetus undergoes considerable stress. Monitoring the mother and fetus in real time or nearly so enables a clinician to intervene if stress increases dangerously. In the example described above results were obtained with a processing delay of ~1 sec.

A variety of parameters may be set up at 64 in FIG. 5 for display and output on a monitor such as 90: e.g.:
i). Patient details for hospital records.
ii). Raw, composite, multichannel abdominal input data (unipolar or bipolar configuration).
iii). Icon for manual or automatic selection of sources of interest e.g. uterine, fetal, maternal.
iv). Projection of data channels on to a subspace spanned by selected sources to eliminate unwanted contributions.
v). Positions of the uterine action potential peaks and bursts of action potentials to be used as fiducial markers.
vi). Frequency spectra of bursts of action potentials relating to each contraction event by windowing contractile bursts.
vii). Marking of fetal movement.
viii). Uterine contractions against instantaneous fetal heartrate.
ix). Uterine contractions against an fECG rhythm strip.
x). Uterine activity in either electrical format or tocodynamometer format.

xi). Criteria, such as Dawes Redman, for fECG to indicate fetal well-being and an alarm to indicate fetal compromise.

xii). Patient record with parameters of interest such as uterine contraction information, fECG rhythm strip and fetal heart rate.

xiii). Database of patient data.

xiv). Zoom facility to focus on fine detail, e.g. structure of heart-beat, heart rate or waveform.

xv). Parameters such as Heart rate variability, ST elevation and other intervals that may be useful in diagnosing fetal well-being in combination with uterine contractions.

Referring now to FIG. 10, a further embodiment 130 of the invention is shown: it is similar to the apparatus 30, and parts previously described are like referenced with a prefix 100 but not described further. It differs to the earlier embodiment 30 only in that in this embodiment 130 a lead box 134 is connected to a transmitter indicated schematically by an antenna 149a communicating with a corresponding receiver indicated by 149b and connected to a computer 136. The transmitter/receiver link from the lead box 134 to the computer 136 enables the lead box 134 to be placed close to or on the patient. Transmitting amplified data in this way enables the screened leads 32 to be shorter than previously: they only need reach the nearby lead box 34. This further reduces scope for noise pick-up and signal loss. In addition, the lack of long trailing leads and their physical connection to the computer 136 enables the mother to be ambulatory, without leads or electrodes having to be disconnected, potentially allowing her to relax more readily when a recording is to be taken.

Referring now to FIG. 11, a further embodiment 230 of the invention is shown: it is similar to the apparatus 30, and parts previously described are like referenced with a prefix 200 but not described further. Each electrode 201 etc. is connected first to a respective pre-amplifier 231 illustrated inset at 233, and each unit 231 is in turn connected to the lead box 234. Suitable pre-amplifiers are well known and will not be described. The pre-amplifiers 231 are disposed adjacent respective electrodes 201 etc. and provide a pre-processing stage. They amplify signals propagating along leads 232, and the signals are therefore larger and (compared to apparatus 30) relatively more immune to electric and magnetic noise sources to which the leads are exposed.

The invention may be used in other applications to monitor stationary and non-stationary muscular activity in other organs, including those of non-human species. Smooth muscle lines the walls of other organs apart from the uterus including the intestine, arteries and veins, bladder, and secretary glands. Its primary role is to regulate the diameter of the organ lumen which it surrounds. Smooth muscle is characterised by a slow speed of contraction and ability to maintain contraction for long periods at low energy cost. It can also be characterised by its innervation (nerve distribution) and propagation properties. The uterus, gut and bladder exhibit few areas of innervation and strong electrical coupling through gap junctions. Therefore this invention may be used for example to monitor bladder function by detecting and classifying an electromyogram of the bladder. This would allow the bladder's detrusor muscle to be assessed for dysfunction, instability, absent or exaggerated reflexes and lack of co-ordination between itself and the urethral sphincter. This method may allow a preliminary non-invasive urodynamic analysis of the patient or indeed provide a non-invasive follow up to an invasive urodynamic test. The characterisation of detrusor and sphincter activity would be particularly useful in various types of incontinence such as:

Nocturnal Enuresis, in the form of an audible patient warning to wake the patient;

Urge Incontinence, to indicate the state of the detrusor and predict involuntary contractions;

Overflow Incontinence, to provide a manual indication of the bladder capacity through resting tone of the detrusor; and Incontinence associated with pregnancy as an indication of bladder capacity.

A similar technique could also be applied to the gut and lower intestine.

The invention claimed is:

1. A method for non-invasive monitoring of electrical muscular activity which is at least partially due to a non-stationary muscular source, the method incorporating the steps of:
   a) providing a blind signal separation technique suitable for separating stationary signals,
   b) placing a plurality of low-noise signal electrodes externally upon a patient's skin for detection of electrical muscular activity, the signal electrodes being localised sufficiently such that:
      i) their muscular signal contributions simulate a single muscular source to the blind signal separation technique despite at least partial non-stationarity of the muscular source, and
      ii) the number of sources detected by the blind signal separation technique is not more than the number of signal electrodes;
   c) using computer apparatus to apply the blind signal separation technique to digital signals derived from signals received from the signal electrodes to separate the muscular source, and
   d) using a display device to display the separated muscular source to a user.

2. A method according to claim 1 wherein the muscular activity is uterine activity.

3. A method according to claim 1 wherein the blind signal separation technique is based on an algorithm of a kind known as an instantaneous algorithm and suitable for addressing blind signal separation problems referred to as instantaneous mixing problems, the instantaneous algorithm incorporating an assumption that signals arrive synchronously at each sensor in a sensor array.

4. A method according to claim 3 wherein the instantaneous algorithm is independent component analysis (ICA).

5. A method according to claim 4 wherein the step of applying the blind signal separation technique applies ICA to processing data derived from signals from the signal electrodes, the data being arranged in successive overlapping blocks such that in pairs of adjacent blocks each subsequent block incorporates a proportion of the data in the respective preceding block, and a correlation scheme is applied to re-order independent sources derived in ICA processing of different blocks to correct for signal swapping.

6. A method according to claim 1 wherein the step of placing the signal electrodes comprises placing four or five signal electrodes at and above navel height with respect to an upright patient at positions close to the expected site of pacemaker activity.

7. A method according to claim 1 wherein the signal electrodes are a first set of signal electrodes and the step of placing the signal electrodes includes placing a second set of signal electrodes upon a patient's skin in positions not localised sufficiently for their muscular signal contributions to simulate a single source to the blind signal separation technique, and wherein the blind signal separation technique employs signals derived via the first set of signal electrodes for monitoring non-stationary muscular activity and signals derived via the first and second sets of signal electrodes for monitoring stationary muscular activity.

8. A method according to claim 7 wherein the non-stationary muscular activity is uterine activity, the stationary muscular activity is cardiac activity and the blind signal separation technique simultaneously acquires uterine activity and maternal and fetal cardiac activity.

9. A method according to claim 8 wherein the blind signal separation technique acquires uterine activity, maternal muscle activity, fetal ECG and maternal ECG.

10. An apparatus for non-invasively monitoring electrical muscular activity which is partly due to a first muscular source which is non-stationary and partly due to a second muscular source which is stationary, characterised in that the apparatus incorporates:
   a) a first set of low-noise signal electrodes for placing externally upon a patient's skin for detection of stationary and non-stationary muscular activity, the first set of low-noise signal electrodes being suitable for localisation sufficiently such that:
      i) their muscular signal contributions associated with the first muscular source will simulate a single stationary source to a blind signal separation technique despite the non-stationarity of the first muscular source, and
      ii) the number of sources detected by the blind signal separation technique will not be more than the number of signal electrodes in the first set thereof;
   b) a second set of low-noise signal electrodes for placing externally upon a patient's skin for detection of stationary muscular activity;
   c) electronic signal processing circuitry for processing signals received from the first and second sets of low-noise signal electrodes into digital signals suitable for application of a computer-implemented blind signal separation technique; and
   d) computer apparatus programmed to implement a blind signal separation technique suitable for separating stationary signals, and to use the technique to:
      i) process digital signals derived from signals received from the first set of low-noise signal electrodes in order to separate non-stationary activity associated with the first muscular source, and
      ii) process digital signals derived from signals received from the first and second sets of low-noise signal electrodes in order to separate stationary activity associated with the second muscular source, and
   e) a display device for displaying the separated muscular source to a user.

11. An apparatus according to claim 10 wherein the non-stationary first muscular source is a uterine source.

12. An apparatus according to claim 10 wherein the blind signal separation technique is based on an instantaneous algorithm.

13. An apparatus according to claim 12 wherein the instantaneous algorithm is independent component analysis (ICA).

14. An apparatus according to claim 13 wherein the computer apparatus is programmed to arrange the digital signals in successive overlapping data blocks such that in pairs of adjacent blocks each subsequent block incorporates a proportion of the data in the respective preceding block, and to apply a correlation scheme to re-order independent sources derived in ICA processing of different blocks to correct for signal swapping.

15. An apparatus according to claim 10 wherein the first set of low-noise signal electrodes comprise four or five signal electrodes for placing at and above navel height with respect to an upright patient at positions close to the expected site of pacemaker activity.

16. An apparatus according to claim 10 wherein the blind signal separation technique is arranged to employ signals derived via the first set of signal electrodes for monitoring uterine activity and signals derived via the first and second sets of signal electrodes for monitoring maternal and fetal cardiac activity.

17. An apparatus according to claim 16 for monitoring uterine activity wherein the blind signal separation technique is arranged to acquire maternal and fetal cardiac activity simultaneously.

18. An apparatus according to claim 16 wherein the blind signal separation technique is arranged to acquire uterine activity, maternal muscle activity, fetal ECG and maternal ECG.

19. An apparatus according to claim 10 wherein the computer apparatus is programmed to:
   a) apply a first filtering procedure to digital signals derived from signals received from the first set of low-noise signal electrodes in order to derive uterine activity, and
   b) apply a second filtering procedure to digital signals derived from signals received from the first and second sets of low-noise signal electrodes in order to derive cardiac activity.

* * * * *